United States Patent
Williamson (10) Patent No.: US 10,302,522 B2
(45) Date of Patent: *May 28, 2019

(54) ASPIRATED SAMPLING SYSTEMS

(71) Applicant: Xtralis Global, Dublin (IE)

(72) Inventor: Alasdair James Williamson, Worthing (GB)

(73) Assignee: Xtralis Global, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/117,810

(22) PCT Filed: Mar. 6, 2015

(86) PCT No.: PCT/EP2015/054760
§ 371 (c)(1),
(2) Date: Aug. 10, 2016

(87) PCT Pub. No.: WO2015/132398
PCT Pub. Date: Sep. 11, 2015

(65) Prior Publication Data
US 2017/0045415 A1 Feb. 16, 2017

Related U.S. Application Data (60) Provisional application No. 61/949,191, filed on Mar. 6, 2014.

(30) Foreign Application Priority Data

Apr. 3, 2014 (AU) .................... 2014901211

(51) Int. Cl.
*G01M 3/28* (2006.01)
*G01N 1/22* (2006.01)
(Continued)

(52) U.S. Cl.
CPC ............ *G01M 3/2815* (2013.01); *G01M 3/20* (2013.01); *G01M 3/207* (2013.01); *G01M 3/222* (2013.01);
(Continued)

(58) Field of Classification Search
CPC ...... G01M 3/2815; G01M 3/20; G01M 3/207; G01M 3/222; G01M 3/243; G01M 3/28;
(Continued)

(56) References Cited

U.S. PATENT DOCUMENTS 5,272,646 A 12/1993 Farmer
8,294,587 B2 * 10/2012 Danz ..................... G08B 17/10
340/517

(Continued)

FOREIGN PATENT DOCUMENTS

AU 2011202538 A1 6/2011
JP 52-61999 A 5/1977
(Continued)

*Primary Examiner* — David Z Huang
(74) *Attorney, Agent, or Firm* — Boyle Fredrickson, S.C.

(57) ABSTRACT

A method for determining correct performance of a sampling pipe in an aspirated particle and/or gas sampling system. The method includes causing a change in airflow in a sampling pipe of the aspirated particle and/or gas sampling system that induces a change in at least one airflow property within the sampling pipe, and detecting an effect of the change in said airflow property. Also disclosed is a method for determining correct performance of an aspirated particle gas sampling system. The method includes determining correct performance of a sampling pipe in the aspirated particle and/or gas sampling and determining correct performance of a detector in the aspirated particle and/or gas sampling system, wherein a test fluid is introduced to the aspirated particle and/or gas sampling system at or near the detector.

22 Claims, 6 Drawing Sheets

(51) Int. Cl.
- *G01N 1/24* (2006.01)
- *G01N 1/26* (2006.01)
- *G01M 3/24* (2006.01)
- *G01M 3/20* (2006.01)
- *G01M 3/22* (2006.01)

(52) U.S. Cl.
CPC .............. *G01M 3/243* (2013.01); *G01M 3/28* (2013.01); *G01M 3/2807* (2013.01); *G01N 1/2247* (2013.01); *G01N 1/2273* (2013.01); *G01N 1/24* (2013.01); *G01N 1/26* (2013.01)

(58) Field of Classification Search
CPC . G01M 3/2807; G01N 1/2247; G01N 1/2273; G01N 1/24; G01N 1/26
See application file for complete search history.

(56) References Cited

U.S. PATENT DOCUMENTS

| | | | | |
|---|---|---|---|---|
| 2003/0061865 | A1* | 4/2003 | Choi | B24B 37/0053 73/49 |
| 2006/0266096 | A1* | 11/2006 | Eickhoff | G01N 27/4163 73/1.06 |
| 2006/0266097 | A1 | 11/2006 | Eickhoff | |
| 2007/0008157 | A1 | 1/2007 | Siemens et al. | |
| 2007/0084286 | A1* | 4/2007 | Ajay | G01F 1/667 73/597 |
| 2010/0050791 | A1* | 3/2010 | Stroup | B01L 3/502 73/864.34 |
| 2012/0079872 | A1 | 4/2012 | Schaefer et al. | |
| 2015/0253165 | A1* | 9/2015 | Ajay | G01F 1/66 73/28.01 |

FOREIGN PATENT DOCUMENTS

| | | |
|---|---|---|
| JP | 56-35900 A | 4/1981 |
| WO | 98/46978 A1 | 10/1998 |
| WO | 2004102499 A1 | 11/2004 |
| WO | 2006/050569 A1 | 5/2006 |
| WO | 2014059479 A1 | 4/2014 |
| WO | 2015054749 A1 | 4/2015 |

* cited by examiner

ASPIRATED SAMPLING SYSTEMS

FIELD OF THE INVENTION

The present invention relates to particle or gas detection systems and in particular to aspirated smoke and/or gas detection systems. However, the invention is not limited to this particular application and other types of sensing systems for detecting target substance in an air volume are included within the scope of the present invention.

BACKGROUND OF THE INVENTION

Aspirated particle or gas detection systems may incorporate a sampling pipe network consisting of one or more sampling pipes with one or more sampling holes, or inlets, installed at positions where smoke or gas may be collected from a region or environment being monitored, which is ordinarily external to the sampling pipe network. Air is drawn in through sampling holes and subsequently along the pipe or pipe network by means of an aspirator or fan and is directed through a particle detector and/or gas analyser at a remote location. Using a pipe network, air may be sampled from a number of different points over an area. Although there are a number of different types of particle or gas detectors which may be used as the detector in a system as outlined above, one particularly suitable form of detector for use in such a system is an optical scatter detector, which is able to provide suitable sensitivity at reasonable cost. An example of such a device is a VESDA® LaserPlus™ smoke detector as sold by the applicant.

To maintain and improve upon the efficiency and effectiveness of an aspirated particle and/or gas sampling system it is essential to ensure the integrity of the sampling pipe network.

One method of testing the integrity of a sampling pipe network involves conducting a smoke test at each sampling hole of the sampling pipe network. If smoke entering each sampling hole is detected at the detector then it can be concluded that the sampling hole and associate pipe network is functioning correctly. This method can be both labour and time intensive.

The present invention provides an improved method of checking a sampling pipe network for correct operation, in particular for testing for fully or partially blocked sampling inlets, broken pipes or the like. Advantageously, the present invention further provides a method and system for centralised integrity check of the sampling pipe network and detector.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The present invention provides a method for determining correct performance of a sampling pipe in an aspirated particle and/or gas sampling system.

In a first aspect the method includes causing a change in airflow in the sampling pipe that induces a change in at least one airflow property within the sampling pipe, and detecting an effect of the change in said airflow property. The change in the air flow property or effect thereof may be transient or persist as long as the change in airflow is maintained.

The sampling pipe preferably extends between a sampling inlet and a detector.

In a preferred embodiment each sampling inlet incorporates a device that when operated causes the change in an airflow property in the sampling pipe.

Detection of a change in flow or pressure by a flow or pressure sensor establishes the integrity of the sampling pipe between the sample inlet and a smoke or gas detector.

The method preferably includes changing a flow direction in the sampling pipe, which causes a valve in the sampling pipe, preferably associated with a sampling inlet, to change state. The method may include detecting a change in flow rate or pressure caused by the changed state of the valve. Advantageously the device is actuated by reversing the flow of air in the sampling pipe i.e. blowing air into the sampling pipe.

In some embodiments the method can include measuring pressure or flow prior to causing a change in airflow in the sampling pipe and in the event the measurement pressure or flow is within predetermined parameters causing said change in airflow.

The method can further include maintaining air in the sampling pipe at a fixed positive pressure to test for leaks in the sampling pipe.

The method can further include causing a pattern of changes in flow or pressure in the sampling pipe to cause a pattern of changes in air flow property.

In one embodiment, the device at each sampling inlet is pneumatically operated.

The sampling pipe may directly connect each sampling inlet to the detector. In one embodiment a plurality of sampling pipes with respective sampling inlets are connected to the detector. The detector may be configured to selectively fluidly connect with the respective sampling pipes. In this embodiment the sensor that detects the effect of the change in air flow property in the sampling pipe can be located in or near the detector.

In an alternate embodiment the sampling pipe may include one or more secondary sampling pipes and the sampling inlets are provided in each of the secondary sampling pipes. In this case it is preferable that each secondary sampling pipe has a sensor to enable independent checking of the performance of each secondary sampling pipe.

The invention also provides a sampling inlet for an aspirated particle and/or gas sampling system, the sampling inlet being configured to direct a flow of air from a monitored region to a sampling pipe of the aspirated sampling system, the sampling inlet being actuatable to cause a change in a flow property in the sampling pipe.

Preferably the sampling inlet includes a flow modifying device, such as a valve, which is actuatable between an open position that is effective when air is drawn into the sampling inlet towards the sampling pipe, and an actuated position, in which the airflow through the sampling inlet has a changed property. Most preferably the flow modifying device is moved into the actuated position by changing the airflow in the sampling inlet. Preferably changing the airflow in the sampling inlet is achieved by reversing the flow direction in the sampling inlet. When the valve is moved to the actuated position the valve may cause an increase in pressure and/or decrease in flow in the sampling inlet. The actuated position may close the sampling inlet. The closure of the sampling inlet can be transient or persistent. The actuated position can be a second open position in which air can flow through the sampling inlet. Preferably the open position defines a first flow path through the sampling inlet, and the actuated position defines an alternative flow path through the sampling inlet. When moving between these positions the flow paths may be blocked, thereby preventing or at least greatly reducing flow through the air sampling system.

The sampling inlet can include multiple actuated positions, for example one closed actuated position and one open actuated position.

Preferably the sampling inlet is biased towards the open position. Movement to the, or each, actuated position can be caused by a change in flow in the air sampling pipe. If multiple actuated positions exist, these may be selected by applying a predetermined change in airflow.

According to a further aspect of the present invention there is provided a method of determining correct performance of a sampling pipe network, e.g. blockage of one or more sample inlets in a sampling pipe network in a particle detection system or breakage or leakage in the system. The method includes blowing air into the sampling pipe network and measuring the flow rate, or pressure, of air through the pipe network. Flow rate can be measured as the blown air is exhausted via at least one sampling inlet in the sampling pipe network. Alternatively, air blown into the pipe network is used to attain a predetermined pressure in the sample pipe network. The method can include detecting a leak on the basis of the pressure measured in the pipe network. The measured flow rate, pressure or rate of change of flow rate or pressure can be compared to a predetermined value or variation, and if the measured value differs from the predetermined value or variation by more than a set amount a fault can be indicated. The air may be blown into the air sampling network from any point either upstream, downstream or intermediate the one or more of the air sampling points. Most preferably, the segment of air sampling pipe being tested is isolated from neighbouring components in the system e.g. by blocking air flow from exiting the segment of the sampling network via any other path except the one or more sampling inlets. The method can additionally include flushing the segment of the sampling pipe being tested by blowing air through the sampling pipe inlets.

Air may be blown into the air sampling network portion from the "detector end" of the air sampling network. In some embodiments the method can include isolating a portion of the air sampling network to enable testing of a specific portion of the air sampling network. Most preferably the method includes causing a valve, or other flow modifying device, at an end of the portion of the air sampling network under test to close change state automatically in response to blowing into the air sampling network.

In some embodiments there is described a method of operating an air sampling system. The method includes operating in a first mode in which the air is drawn into the air sampling system from the area being monitored and one or more sampling inlets of the air sampling system are in a first state. The method also includes operating in a second mode in which flow is reversed in the air sampling system compare to the first mode so as to cause sufficient pressure in the air sampling system to cause an air sampling inlet to operate in an actuated state. Preferably the second mode has a different flow characteristic to the first mode. The actuated state can be an open, closed or partly closed state. The method can further include operating in a third mode in which flow is reversed in the air sampling system compared to the first mode so as to cause sufficient pressure in the air sampling system to cause an air sampling inlet to operate in a second actuated state. Preferably the third mode has a different flow characteristic to the second mode. The second actuated state can be an open, closed or partly closed state.

The method can include cycling between the second and third modes.

The method can include measuring the pressure or flow of air in at least part of the sampling pipe network in any one or more of the first, second or third states to determine a fault in the sampling pipe network. The method can include flushing the at least part of the sampling pipe network in at least one of the second or third modes. The flushing can be performed by reversing flow in the sampling network compared to the first mode.

According to a further aspect of the invention there is provided a method for centralised integrity testing of an aspirated particle or gas detection system. The method includes testing the integrity of the sampling pipe network and sampling holes in accordance with any of the aspects and embodiments of the invention described above. Furthermore, the invention includes testing the operation of the detector by introducing a test fluid at the detector.

Preferably means to introduce a test fluid to the detector is located at or near the detector and in one embodiment is operated by the controller. In a preferred embodiment the means to introduce a test fluid is a smoke generator but it will be appreciated the test fluid may also be a gas or other particulate laden fluid. Accordingly, the controller is operable to control the aspirator in order to cause a change in airflow in the sampling pipe to induce a change in at least one airflow property within the sampling pipe, as described above, and is also operable to control the smoke generator to test the correct operation of the smoke detector. Correct operation of the detector is determined when a predetermined level of smoke is detected by the detector.

The controller may be operated manually or automatically. Preferably the method for centralised integrity testing of the aspirated particle or gas detection system, and testing of the operation of the detector, is undertaken automatically by the controller. For example, automatic testing may be performed on a periodic basis, for example every month.

In an alternate embodiment it will be appreciated that a test fluid such as smoke, gas, or other particulate laden fluid may be manually introduced into the detector, i.e. smoke may be manually sprayed through a port directly into the detector.

This aspect of the invention enables the whole sampling pipe network, sampling holes, and detector to be tested centrally and avoids manual smoke testing of each sampling hole. The fully automated method permits full integrity testing of the aspirated particle or gas detection system which is particularly advantageous when the detection system is located in a difficult to access area.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

The invention will now be described, by way of example only, with reference to the accompanying drawings in which.

DETAILED DESCRIPTION OF THE EMBODIMENTS

Figure 1:
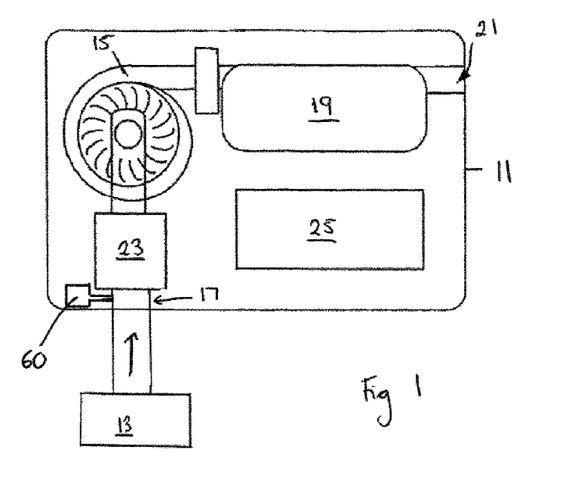
FIG. 1 is a schematic representation of a particle detector in accordance with an embodiment of the invention.

FIG. 1 shows a particle detector 11 of a particle or gas detection system. In this embodiment the detector is a particle detector 11 in the form of a smoke detector. The detector 11 is in fluid communication with a sampling network 13. The sampling network 13 may take the form of those shown in FIG. 2 or 3 for example. The configuration of these sampling networks will be discussed in further detail below.

An aspirator 15 draws air into the sampling network 13 through inlet 17 and along into a particle detection chamber 19. The air sample exits the detection system through outlet 21.

The detector 11 includes a flow sensor 23. In a preferred embodiment of the present invention, an ultrasonic flow sensor as described in WO 2004/102499 is employed. This sensor enables volumetric flow measurements to be made. The flow sensor 23 provides an indication of the volume of air flowing into the particle detector 11 from the sampling network 13 per unit time. The output of the flow sensor 23 may be used to infer, for example, when flow faults e.g. a blockage of the sampling network 13 or reduced aspirator performance, has occurred.

The particle detector 11 also includes a controller 25 for determining the level of particles in the air sample based on the detector's 19 output and apply alarm and/or fault logic to the detector output, to alert a user to the presence of particles and the operating state of the system. A typical installation of a Vesda or ICAM smoke detector, from Xtralis Pty Ltd. would be an example of a system of this type.

The particle detector 11 may also include means 60 to introduce a test fluid to the detector 19. In the embodiments that follow means 60 preferably takes the form of a smoke generator. The smoke generator 60 is advantageously located downstream of the sampling pipe network 13 and upstream of the aspirator 15. Preferably the smoke generator is located upstream of the flow sensor 23. The smoke generator 60 is illustrated as part of detector 11 but it will be appreciated that the smoke generator 60 may be located external to the detector 11 at or near the inlet 17, or downstream of the flow sensor 23. It will also be appreciates that smoke may be manually sprayed through a port (not illustrated) into the detector instead of using smoke generator 60.

Figure 2:
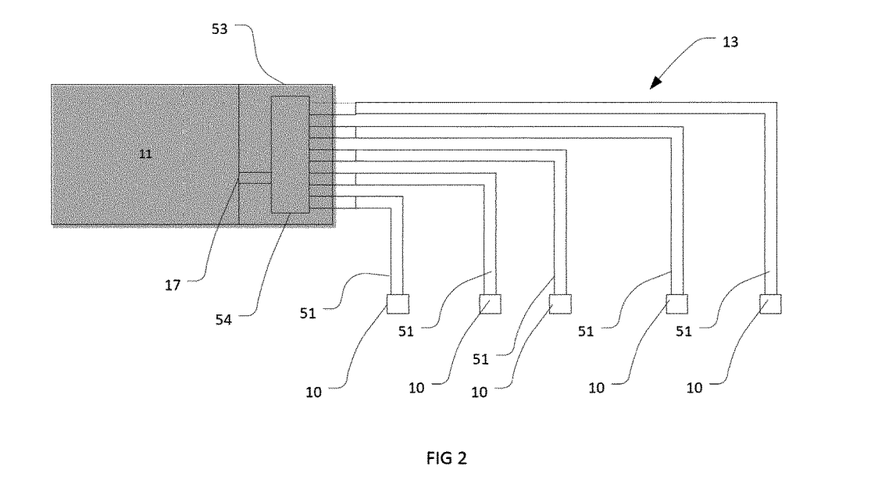
FIG. 2 is a schematic representation of a sampling network according to an embodiment of the invention.

Referring to FIG. 2 there is illustrated a multi-channel sampling network 13 including a plurality of sampling pipes 51 fluidly connected to a manifold 53. Outlet port 55 in manifold 51 directs air flow from the manifold 53 to particle detector 11. For clarity the internal components of the detector 11 are not shown, but are as described in connection with FIG. 1. A rotary valve 54 may be employed to selectively connect each of the sampling pipes 51 to the manifold 53. An example of such a detector and rotary valve set up can be found in the ICAM IFT-15 smoke detector by Xtralis. Each sampling pipe 51 is in fluid communication with the external environment via respective sampling inlets 10 which will be discussed in greater detail below.

Figure 3:
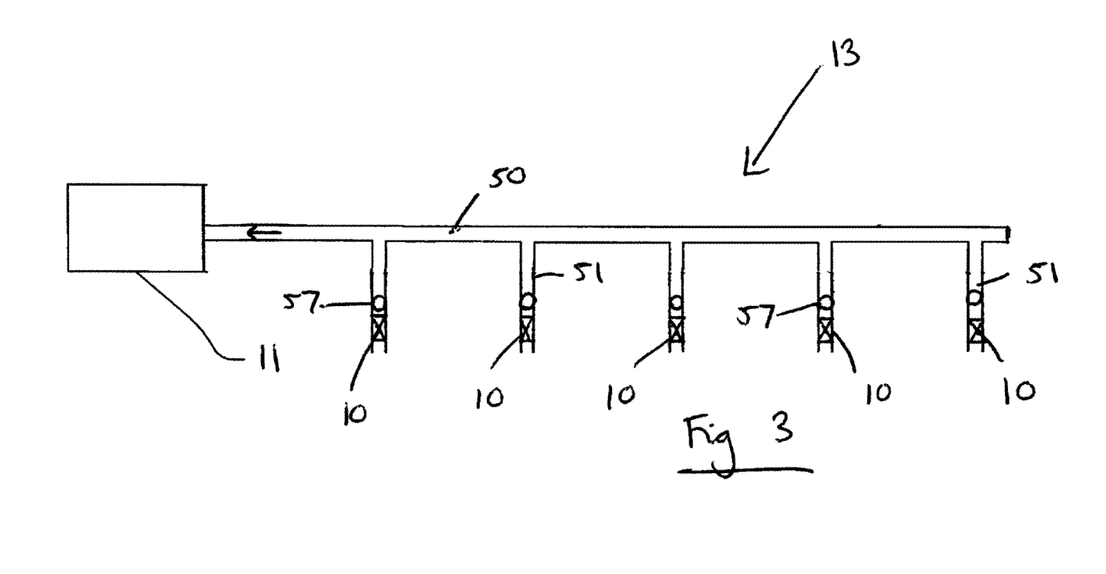
FIG. 3 is a schematic representation of a sampling network according to another embodiment of the invention.

An alternate configuration of a sampling network is illustrated in FIG. 3. As in FIG. 2 the sampling network 13 shown includes a plurality of sampling pipes 51. In this embodiment each of the sampling pipes 51 are in turn fluidly connected to a primary sampling pipe 50 which directs air flow from all of the sampling pipes 51 to the detector 11. As in FIG. 2, each sampling pipe 51 is in fluid communication with the external environment via respective sampling inlets 10. In this embodiment additional flow or pressure sensors 57 may be provided within each sampling pipe 51 adjacent to or within each sampling inlet 10 as described below.

Referring to FIGS. 4 to 7 there is illustrated a sampling inlet 10 of a smoke and/or gas sampling system. Sampling inlet 10 includes a housing 12 that is typically installed in a roof tile, ceiling, or other bulkhead 14. Housing 12 includes a flange 3 that prevents the housing from being pushed through a ceiling out of the monitored area. Housing 12 is generally cylindrical and includes air inlet 16 and air outlet 18. Air inlet 16 is open to the surrounding environment and allows sample air to be drawn in and through the sampling inlet 10 to air outlet 18. Air outlet 18 is in turn connected to a sampling pipe 51 which directs the sampled air to a detector 11.

Sampling inlet 10 includes a central chamber 20 defined by wall 22 in between the air inlet 16 and air outlet 18. The lower end 24 of air outlet 18 extends to the upper section of the chamber 20 as best shown in FIG. 3. The lower end 24 of the air outlet 18 is in turn surrounded by wall 26 of the housing 12. Wall 26 is radially spaced from the air outlet 18 thereby defining a recess 28 which will be described further below.

Figure 4:
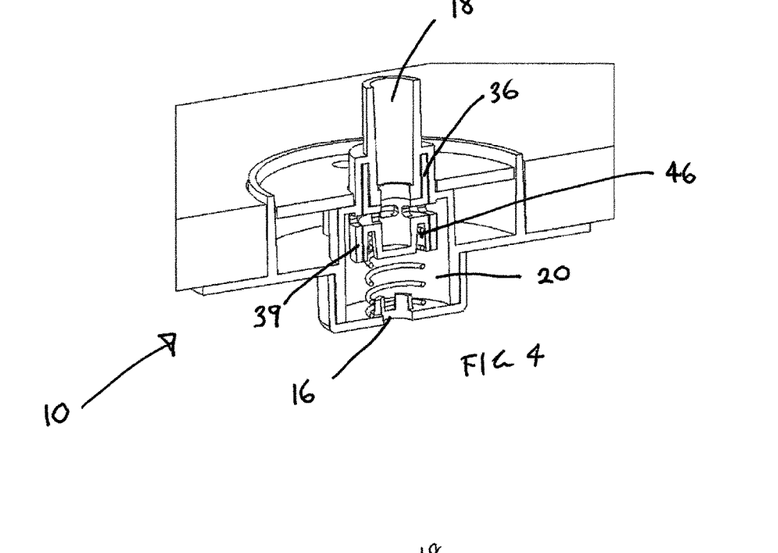
FIG. 4 is a cross-sectional view of a sample inlet in accordance with an embodiment of the invention shown in its normal operational configuration.
Figure 5:
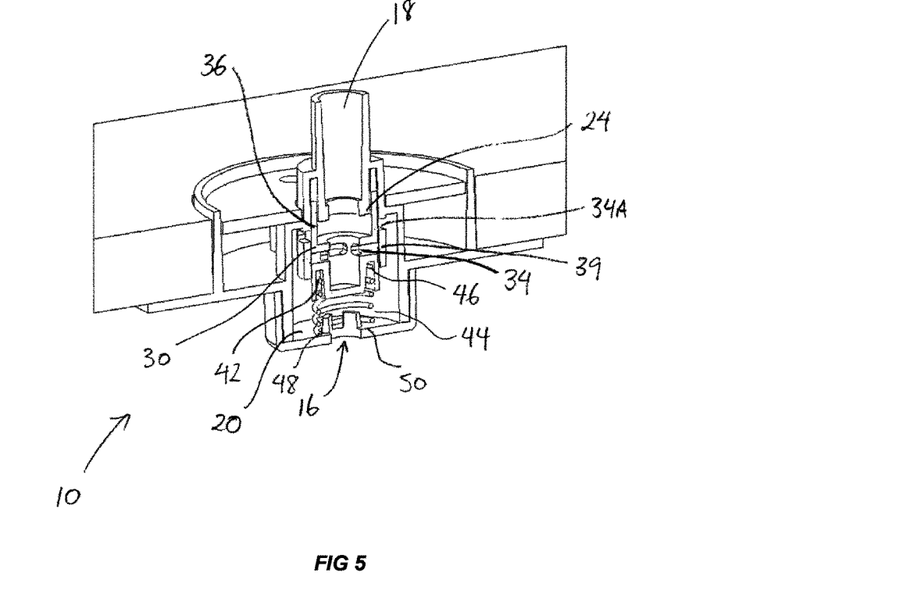
FIG. 5 is a cross-sectional view of the sample inlet of FIG. 4 shown in a closed configuration.
Figure 6:
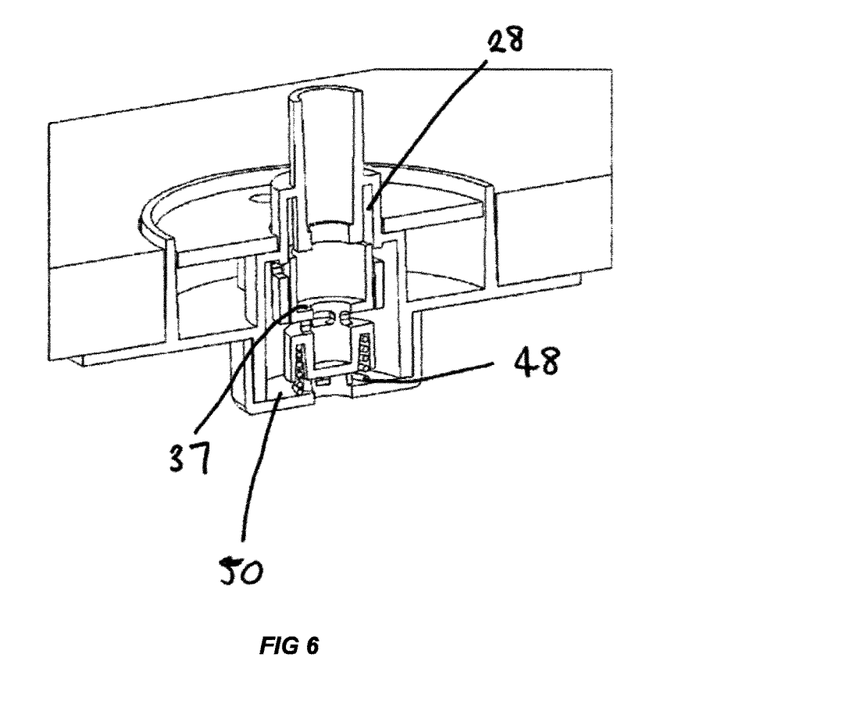
FIG. 6 is a cross-sectional view of the sample inlet of FIG. 4 shown in its actuated configuration.
Figure 7:
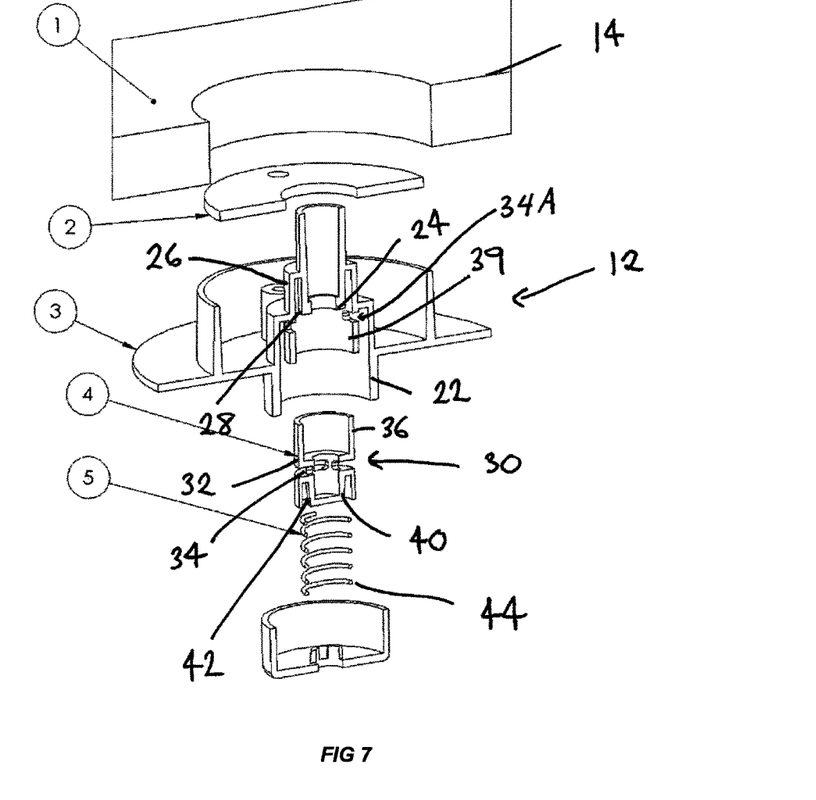
FIG. 7 is an exploded cross-sectional view of the sample inlet of FIG. 4.

Chamber 20 houses a generally cylindrical shuttle 30 that is movable between a normal operational position shown in FIG. 4 and an actuated position, as shown in FIG. 6, passing through a closed position shown in FIG. 5. The shuttle operates as a flow modifying device within the sampling inlet 10 as described below. In this case is operates as a valve, which in this case has two open positions with a closed position between them. The shuttle 30 has an external cylindrical wall 32 that includes one or more apertures 34 that permit the passage of air therethrough. The upper end 36 of shuttle 30 is adapted to be received in recess 28 when the shuttle is in its normal operational position. The lower end 24 of air outlet 18 forms an airtight seal with landing 37 of the shuttle 30.

The lower end 24 of the shuttle 30 is surrounded by and supported within cylindrical wall 39.

The lower end 38 of shuttle 30 includes an additional wall 40 spaced internally radially of wall 32 thereby defining a further recess 42.

Shuttle 30 is biased into its normal, operational position by means of spring 44 on which shuttle 30 is mounted. The upper end 46 of spring 44 is received within recess 42, while the lower end 48 of spring 44 is connected to the base 50 of chamber 20. As shown in FIG. 6, spring 44 is compressed when the shuttle 30 is in its actuated position.

Figure 8A:
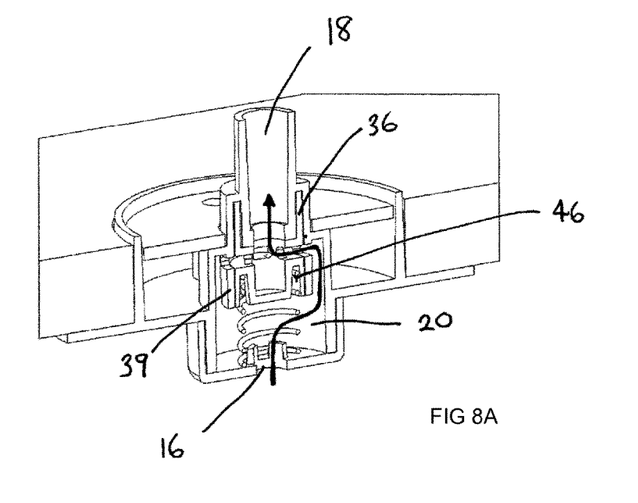
FIGS. 8A and 8B show the sample inlet of FIG. 4 and respectively illustrate the first and second flow paths through it.

In normal operation of the air sampling system, air is drawn under negative pressure by an aspirator into the sampling inlet 10 via air inlet 16 into chamber 20. The sampled air is then drawn through apertures 34A in the wall 39 and into apertures 34 which align with apertures 34A in this position. The air is thus drawn into the interior of the shuttle 30 and directly through the air outlet 18 to a sampling pipe 51 and to a detector 11. This first flow path is illustrated in FIG. 8A. The flow sensor 23 of the particle detector 11 can be used to determine if the sample flow is within predetermined parameters. If a sufficiently sensitive flow sensor is used, the flow sensor 23 can be used to determine whether there are one or more blocked sampling holes or sampling pipes. In the example of FIG. 2, should a flow restriction be detected, the rotary valve 54 can be used to selectively couple the sampling pipes 51 to the detector individually or in groups to enable identification of which pipe or pipes 51 or their associated sampling inlet 10 might be blocked.

When it is desired to test the operation of the sampling system, in particular to test the integrity of a sampling pipe 51, air flow in the sampling pipe 51 is reversed. This may be achieved by reversing the aspirator 15 or operating a series of valves that redirect flow back into the sampling pipe 51 at the detector-end of it, so that air is blown into the sampling pipe 51 from the detector end. In this condition positive pressure is built within the sampling network and sampling inlet 10.

Referring to the embodiment illustrated in FIG. 2 rotary valve is preferably employed to select which of the sampling pipes 51 air is blown into from the aspirator 15. Each sampling pipe may be tested in sequence for example. Alternatively a plurality of sampling pipes 51 can be tested simultaneously by setting the rotary valve 54 in a mode where the aspirator 15 is in fluid communication with a plurality (perhaps all) sampling pipes 51 at the same time. This simultaneous testing mode may be used initially, followed by the sequential testing of smaller groups (or individual pipes) to search for the source of flow faults.

With regard to the embodiment illustrated in FIG. 3 air is blown into primary sampling pipe 50 and into respective sampling pipes 51. Valves may be provided to selectively connect each of the sampling pipes 51 to the primary sampling pipe 50, so that a selected branch or portion of the air sampling network can be isolated and separately tested. Alternatively, an additional local flow or pressure sensor 57 is provided within each of the sampling pipes 51 adjacent to or within each sampling inlet 10 of the embodiment illustrated in FIG. 3. The local sensor 57 is configured to signal to the detector 11, through a wired or wireless network, the presence or level of air flow or pressure in the branch of the sampling network. This enables the detection of a localised flow fault in the sampling tube 51 that would not necessarily alert the primary flow sensor 23.

When air is being blown into the sampling pipes 51, air enters the sample inlet 10 via the air outlet 18. This causes pressure to build in the sampling network, which causes the shuttle 30 to compress spring 44 and the shuttle 30 to move downwardly. As the shuttle 30 moves downwardly, wall 39 blocks apertures 34 in the shuttle 30 thereby stopping air flow. This closed condition is shown in FIG. 5. The shuttle can be maintained in this position by maintaining the air pressure in the system at a predetermined level.

In this state the sampling pipe network 13, or portion under test, can be tested for holes or breaks or other conditions that enables a loss of pressure in the sampling network when the sampling inlet(s) 10 are in the closed actuated state. This test is performed in several ways, e.g. by measuring the pressure in the sampling pipe network over time, measuring the rate at which the aspirator needs to operate to maintain the pressure at a predetermined level (e.g. in terms of fan speed, electrical load on the aspirator or any other suitable measure), measuring flow in the sampling pipe network 13, or portion under test (where a zero flow will indicate pipe integrity).

Figure 8B:
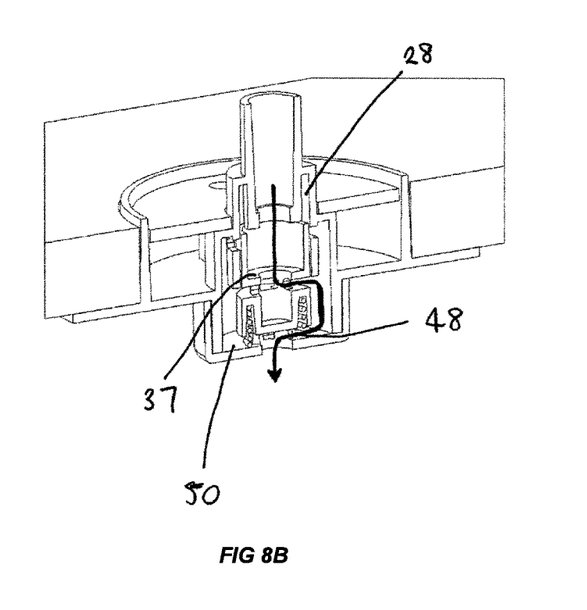

As the shuttle 30 moves further downwardly the apertures 34 become open again and air flow through the chamber 20 resumes. With the shuttle 30 in this actuated position as shown in FIG. 6, air flows out of apertures 34 and then out of the air inlet 16 to the surrounding environment. Upstanding lugs 19 or similar are provided around the perimeter of the air inlet 16 and act as a stop to prevent the shuttle 30 from sealing the air inlet 16. This second flow path is illustrated in FIG. 8B. The pressure at which sampling point 10 reaches this actuated position will, in the present example, be higher than the pressure at which the sampling point reaches the closed actuated position of FIG. 5. In this open actuated position the reverse flow through the sampling network 13 can be used to flush the sampling pipes 51. Any loose material, such as dust or lint may in this way be blown out of the sampling inlets 10.

In some embodiments pressure can be maintained in the sampling pipe at or near a threshold pressure at which the shuttle 30 is pushed to its furthest point of travel such that the apertures 34 are fully open, the compression in the spring may overcome the downward pressure caused by the air being blown in the sampling pipe 51, this causes the shuttle 30 to "bounce" upwardly back towards its normal operational position as shown in FIG. 4. If the aspirator is still blowing air into the sampling pipe 51 to again reach the threshold pressure, the shuttle 30 is again forced to compress spring 44 and move to its actuated open position. This process effectively modulates the air flow rate/pressure that is detected by flow or pressure sensor 23. A single interruption to the air flow rate will be sufficient for the flow or pressure sensor 23 to establish the presence of the shuttle 30 in the sampling inlet 10 and its correct operation. If no interruption to the air flow is sensed by the flow sensor 23 then it signals to the controller 25 that there is a flow fault with either the sampling pipe 51 or sampling inlet 10. Advantageously, the present invention is able to detect whether the sampling inlet 10 itself has become detached from the sampling pipe 51 since there will be no change in air flow or pressure detected by the flow sensor 23.

As will be appreciated any break or leak in the sampling network 51 will change the behaviour of the sampling inlet when air is blown into the sampling pipe 51, and thus cause the flow/pressure detected by the flow/pressure sensor to deviate from that expected. For example, is a pipe 51 is broken the shuttle may not move at all since pressure will be released from the break instead of causing the shuttle to move. A lesser leak may cause a slower decrease in flow rate or increase in pressure than expected, which may also be detectable.

In a some embodiments, the sampling inlet can cause the air flow and/or pressure to be modulated at a certain frequency detectable by the flow sensor or pressure sensor. This may require modulating the operation of the aspirator to trigger the operation of the sampling inlet. This offers the advantage of being able to detect faults with the sampling inlet itself for example if the sampling inlet is partially blocked the shuttle may stick and have a longer period of oscillation than expected.

In some systems the sample inlet 10 can include an indicator to signal to a technician of a fault. For example the sample inlet 10 can include an electrical circuit e.g. in the form of circuit board 2, which incorporates a visual and/or audible signalling device to indicate a fault. In addition or alternatively the indicator can indicate an alarm or any other condition of the smoke and/or gas detection system.

In some systems the sample inlet 10 can include an elastomeric valve to determine the flow characteristics of the sample inlet. A suitable elastomeric valve may take the form of a diaphragm or disc of elastomeric material with a slit cut through it to define flaps. When air pressure is applied to the valve the slits will open in a pre-determined manner to allow airflow therethrough. As will be appreciated, diaphragm valves of this type are well known and their air flow control properties can be chosen by one skilled in the art.

In other embodiments, the sample inlet 10 is actuated by electrical, magnetic, or other means.

The circuit can be powered in any way, e.g. by battery, remote power supply, signalling system or energy harvesting means, that derives power from the environment, e.g. solar power, or via air movement.

Referring to FIG. 1, when it is desired to test the operation of the detector 19, controller 25 operates smoke generator 60 to generate a predetermined level of smoke. Smoke is drawn via the aspirator 15 through the flow sensor 23 and into detector 19. In the event that the flow path between the smoke generator 60 and the detector 19 is compromised, e.g. due to a broken or blocked pipe, or faulty aspirator, the detector will not detect the predetermined level of smoke and a fault will be indicated. Similarly, if the flow path is not compromised but the detector is faulty, the detector will not detect the predetermined level of smoke and a fault can be indicated.

In combination with the method of testing the integrity of the sampling pipes and sampling inlets described above, testing the operation of the detector with a smoke generator at the detector enables complete monitoring and centralised maintenance of the entire particle or gas detection system.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for determining correct performance of an aspirated particle and/or gas sampling system, the method including:
   determining correct performance of a sampling pipe in the aspirated particle and/or gas sampling system by:
   causing a change in airflow in a sampling pipe of the aspirated particle and/or gas sampling system that induces a change in at least one airflow property within the sampling pipe, wherein the change in airflow is caused by changing a flow direction of air in the sampling pipe;
   detecting an effect of the change in said airflow property; and
   determining correct performance of a detector in the aspirated particle and/or gas sampling system, wherein a test fluid is introduced to the aspirated particle and/or gas sampling system at or near the detector.

2. The method of claim 1, wherein the test fluid is introduced into the detector.

3. The method of claim 2, wherein the test fluid is smoke.

4. The method of claim 3, wherein correct operation of the detector is determined when a predetermined level of smoke is detected by the detector.

5. The method of claim 2, which further comprises using a smoke generator to introduce the test fluid.

6. The method of claim 1, which further comprises:
   establishing the integrity of the sampling pipe between a sample inlet and a smoke or gas detector by detecting flow or pressure within the sampling pipe.

7. The method of claim 1, wherein a plurality of sampling pipes with respective sampling inlets are connected to the detector and the method includes selectively fluidly connecting the respective sampling pipes to the detector and detecting the effect of the change in air flow property in the sampling pipe connected to the detector.

8. The method of claim 1, wherein the sampling pipe includes one or more secondary sampling pipes and sampling inlets are provided in each of the secondary sampling pipes, and wherein each sampling inlet incorporates a device that, when operated, causes the change in an airflow property in the sampling pipe.

9. The method of claim 1, wherein:
   changing the flow direction in the sampling pipe causes a valve to change state.

10. The method of claim 9, wherein detecting an effect of the change in said airflow property includes detecting a change in flow rate or pressure caused by the changed state of the valve.

11. The method of claim 1, which further comprises:
    maintaining air in the sampling pipe at a fixed positive pressure to test for leaks in the sampling pipe.

12. A method for determining correct performance of an aspirated particle and/or gas sampling system; comprising a sampling pipe network and at least one gas or particle detector, the method including:
    determining correct performance of a sampling pipe in the sampling pipe network by a method comprising changing a flow direction of air in the sampling pipe by blowing the air into the sampling pipe network and measuring the flow rate, or pressure, of the air blown through the sampling pipe network, and
    determining correct performance of a detector in the aspirated particle and/or gas sampling system, wherein a test fluid is introduced to the aspirated particle and/or gas sampling system at or near the detector.

13. The method of claim 12, which further comprises:
    measuring flow rate as the blown air is exhausted via at least one sampling inlet in the sampling pipe network.

14. The method of claim 12, wherein air blown into the sampling pipe network is used to attain a predetermined pressure in the sampling pipe network, and wherein the method further comprises:
    detecting a leak on the basis of the pressure measured in the sampling pipe network.

15. The method of claim 12, wherein measured flow rate, pressure or rate of change of flow rate or pressure is compared to a predetermined value or variation, and, if the measured value differs from the predetermined value or variation by more than a set amount, a fault can be indicated.

16. The method of claim 12, which further comprises:
    testing a segment of the sampling pipe network using a method that includes isolating the segment of the sampling pipe network being tested from neighbouring components in the system.

17. The method of claim 16, further comprising flushing the segment of the sampling pipe network being tested by blowing air through at least one sampling inlet.

18. The method of claim 16, wherein air is blown into the segment of the sampling pipe network from a detector end of the sampling pipe network.

19. The method of claim 16, which further comprises:
    causing a valve, or other flow modifying device, at an end of the segment of the sampling pipe network under test to change state automatically in response to blowing into the sampling pipe network.

20. The method of claim 12, wherein the test fluid is smoke.

21. The method of claim 20, which further comprises using a smoke generator to introduce the test fluid.

22. The method of claim 21, wherein correct operation of the detector is determined when a predetermined level of smoke is detected by the detector.

* * * * *